United States Patent
Rode et al.

(10) Patent No.: US 6,315,719 B1
(45) Date of Patent: Nov. 13, 2001

(54) SYSTEM FOR LONG-TERM REMOTE MEDICAL MONITORING

(75) Inventors: Wilfried Rode, Sottrum; Rolf Klintworth, Delmenhorst; Klaus-Peter Ludwig, Ueberlingen, all of (DE); Michael Oberle, Zurich (CH)

(73) Assignee: Astrium GmbH, Ottobrunn (DE)

( * ) Notice: Subject to any disclaimer, the term of this patent is extended or adjusted under 35 U.S.C. 154(b) by 0 days.

(21) Appl. No.: 09/603,853

(22) Filed: Jun. 26, 2000

(30) Foreign Application Priority Data

Jun. 26, 1999 (DE) .............................. 199 29 328

(51) Int. Cl.[7] ....................................................... A61B 5/00
(52) U.S. Cl. ..................... 600/300; 128/903; 600/300; 600/301; 600/368; 600/382; 600/390; 600/391; 600/393; 600/483; 600/484; 600/485; 600/509; 600/532; 600/544; 607/60
(58) Field of Search ................................... 600/509, 300, 600/301, 382, 386, 390, 391, 393, 483, 513, 534, 481; 607/149, 60; 128/903; 434/258

(56) References Cited

U.S. PATENT DOCUMENTS

| 4,625,733 | * | 12/1986 | Saynajakangas | 128/687 |
|---|---|---|---|---|
| 4,987,897 | * | 1/1991 | Funke | 128/419 |
| 5,335,664 | * | 8/1994 | Nagashima | 128/696 |
| 5,511,553 | * | 4/1996 | Segalowitz | 128/696 |
| 5,957,854 | * | 9/1999 | Besson et al. | 600/509 |
| 5,959,529 | * | 9/1999 | Kail, IV | 340/539 |
| 6,015,386 | * | 1/2000 | Kensey et al. | 600/486 |
| 6,028,514 | * | 2/2000 | Lemelson et al. | 340/539 |
| 6,076,016 | * | 6/2000 | Feierbach | 607/32 |
| 6,102,856 | * | 8/2000 | Groff et al. | 600/301 |

FOREIGN PATENT DOCUMENTS

| 19607222 | 8/1997 | (DE) . |
| 0880936 | 12/1998 | (EP) . |

OTHER PUBLICATIONS

"Transponder–EKG", by M. R. Bedrich, Biomed. Technik vol. 42, No. 4, Apr. 1997, pp. 90–92.

\* cited by examiner

Primary Examiner—Jeffrey R. Jastrzab
Assistant Examiner—Frances P Oropeza
(74) Attorney, Agent, or Firm—W. F. Fasse; W. G. Fasse

(57) ABSTRACT

A system for long-term remote medical monitoring is especially suitable for the medical supervision of astronauts onboard a space station. The system includes at least one autonomous sensor unit (SU) with a sensor (1) and transmit/receive electrodes (2) connected to a microchip (3) and mounted on a carrier (4) in the form of an adhesive bandage that can easily be applied to the skin of the subject astronaut (11). The system further includes a body transceiver (10) that is worn on the body of the subject and acts as a centralized transmitting and receiving unit, and a portable data logger (12). Medical data such as the pulse rate and the like, as well as environmental data such as the ambient surrounding air temperature, are sensed by respective allocated sensor units (SU) and transmitted from the sensor units as electrical signals via the skin and other body tissues of the subject (11) to the body transceiver (10). From the body transceiver (10), the data signals are further transmitted, for example by a radio or infrared transmission, to the data logger (12), where the data can be recorded, displayed, processed, or further transmitted via a satellite (14) to a base station (13) or a ground-based facility such as a hospital (15). Polling signals are also transmitted from the body transceiver (10) to the sensor units (SU) in a wireless manner through the skin and other body tissues of the subject.

15 Claims, 3 Drawing Sheets

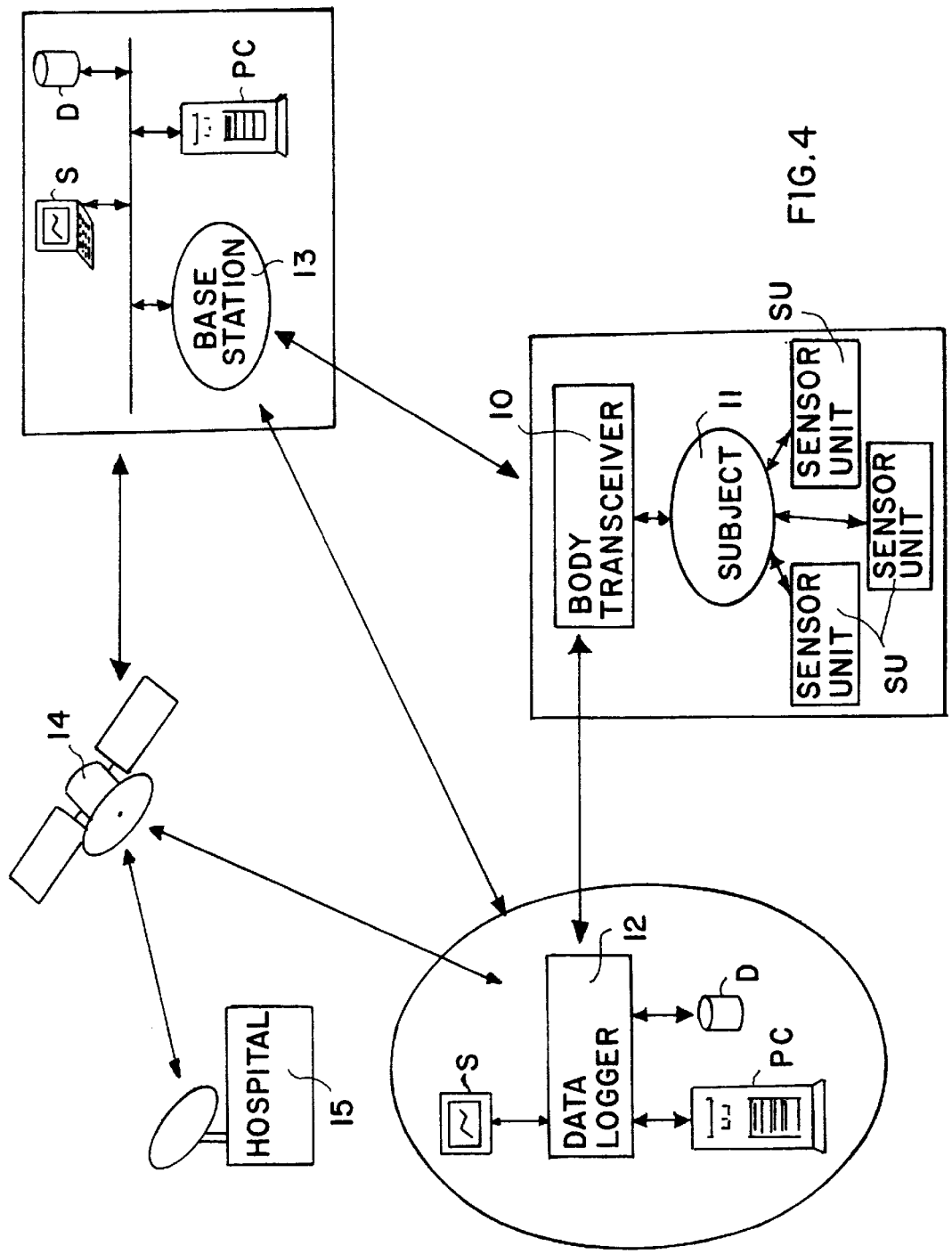

SYSTEM FOR LONG-TERM REMOTE MEDICAL MONITORING

PRIORITY CLAIM

This application is based on and claims the priority under 35 U.S.C. §119 of German Patent Application 199 29 328.7, filed on Jun. 26, 1999, the entire disclosure of which is incorporated herein by reference.

FIELD OF THE INVENTION

The invention relates to a method and an apparatus for remotely carrying out a long-term medical monitoring, especially for carrying out the medical monitoring and supervision of astronauts onboard a space station, which uses sensors arranged directly on the skin surface of the subject to be monitored, as well as a data recording unit associated with the sensors.

BACKGROUND INFORMATION

Astronauts onboard space stations, and particularly the International Space Station (ISS), must live and work under extreme external conditions for rather long time periods, of several weeks, months, or even years. For the personal protection of these astronauts, as well as the supervision and assurance of the success of the overall mission, it is therefore necessary to carry out a continuous monitoring of the medical or physical conditions of these astronauts.

The medical monitoring system to be used in the above-mentioned context must be small, portable, and operable by a single astronaut to which the system is connected. The monitoring of the physical or medical data provided by the respective sensors must be possible continuously while the astronaut is at any location within the space station, and also while the astronaut is carrying out extra vehicular activities (EVAs) outside of the space station. Thus, the system requires a remote monitoring capability. Moreover, such a system must be easily integratable into the already existing telecommunication infrastructure of the space station.

Such a remote medical monitoring system is also becoming the subject of increased interest in fields other than space medicine, such as in the fields of emergency medicine, sports medicine and leisure activity medicine, as well as for the real-time physical monitoring of persons engaging in sports and leisure time activities, for monitoring the overall fitness or the actual existing physical load being applied to or exerted by a person. In such fields, there is an ever increasing demand for the miniaturization of medical devices such as electrocardiographs (EKG) or pulse oximeters, for carrying out the medical monitoring functions, in order to achieve the greatest possible portability of such devices, and to make the use of such devices suitable in the greatest range of applications.

A range of devices already exists for carrying out such purposes, for example in the form of portable transient recorders. However, any such known devices or systems are essentially limited to the detection and monitoring of relatively few biomedical signals. The number of the sensors utilized in such systems is thus also comparatively limited, and the signal transmission of the biomedical signals from the sensor to a connected data logger as well as to a possibly provided process computer, is typically hard-wired, i.e. carried out by wire-based connections. In other words, the respective sensors are connected to the other evaluating, processing and recording devices by means of hard wired connections. If additional signals are to be measured, then the devices correspondingly become larger, or an additional data recorder must be used. For these reasons, the known devices and systems are not suitable, or can only be used with serious limitations, for an encompassing, location-independent, user-friendly, remote telemonitoring of a broad range of physical and/or medical parameters. Furthermore, such known systems are not well suited to be being reactively adapted to flexible and varied demands of the system.

SUMMARY OF THE INVENTION

In view of the above, it is an object of the invention to provide a system, and more particularly a method and an apparatus, for the long-term remote medical monitoring of persons or other living subjects (e.g. zoo animals or animals in the wild), which system makes it possible to use a flexible arrangement of various different autonomous sensors at various different desired locations on the body of the subject, simultaneously, for carrying out an adaptable continuous monitoring of various different physical and/or medical parameters of the subject. It is a further object of the invention to provide such a system that is suitable as a general adaptable and encompassing monitoring system that can readily be integrated into existing electronics and telecommunication infrastructures, and particularly is suitable for remote monitoring of physical and medical data by means of satellite communication. The invention further aims to avoid or overcome the disadvantages of the prior art, and to achieve additional advantages, as are apparent from the present specification.

The above objects have been achieved according to the invention in a system for long-term remote medical monitoring of a person or other subject, such as an astronaut onboard a space station. The system according to the invention comprises at least one autonomous sensor unit including a sensor and a pair of transmit/receive electrodes that are adapted to be arranged on the skin or body surface of the subject, a central transmitting and receiving unit which is adapted to be arranged on the body of the subject, and a portable data recording unit. The autonomous sensor units are adapted to acquire sensor data from the body of the subject, i.e. medical and/or physical data such as pulse rate, blood oxygen content, blood glucose content, other blood composition data, blood pressure data, electrocardiogram data, electroencephalogram data, respiration rate data, perspiration data, body temperature data, and the like. The transmit/receive electrodes of each autonomous sensor unit are adapted to transmit the acquired sensor data into the body of the subject, so that these sensor data are transmitted via the skin and/or other body tissues of the subject to the central transmitting and receiving unit. Other signals, such as monitoring signals and polling signals can be transmitted from the central transmitting and receiving unit through the body tissues of the subject to the sensor unit, where these signals are picked up by the transmit/receive electrodes of the respective sensor unit.

Particularly, the sensor data are transmitted through and received from the skin and other body tissues of the subject body in the form of electrical alternating current (a.c.) voltage signals that are conducted through the body tissues. As a result, the present system does not require any additional cable or hard wire connection, or even a radio link connection for transmitting the sensor data from the autonomous sensor units to the central transmitting and receiving unit and other components of the system, since the sensor data are directly exchanged via the skin and other body tissues of the subject. This has the advantage that the sensors may be adaptably arranged at any desired location on the body of the subject, whereby the sensors are automatically connected to the required electrical conductor for achieving the signal transmission, i.e. the signal transmission is carried out through the electrical conductor provided by the skin and other body tissues of the subject.

Such a body-based data transmission additionally has the advantage that the transmitting power required therefore is extremely small. This avoids the generation of interference in the electrical operation of other devices, and also helps to prevent the unintended interception or tapping and surveillance of the sensitive medical data. The resulting very low power consumption is additionally advantageous for achieving the goal of a long-term monitoring, especially in applications having a limited power supply.

Further preferred features of the invention call for the use of highly miniaturized components in the inventive system, which improves both the wearing comfort and the user-friendly operation of the system components. Furthermore, a rather large plurality of sensors (e.g. 20 or 30 or even more) can be simultaneously used with the system, without significantly reducing the wearing comfort and the ease of operation. The system makes it possible to simply and quickly remove sensors from the system or add additional sensors to the system. The number of sensors can be changed without requiring an additional central transmitting and receiving unit, i.e. a so-called body transceiver, and without requiring a varied or changed construction of the overall system.

Moreover, different types of sensors, i.e. different sensors for acquiring different medical or physical data from the subject, can be used simultaneously in the system, whereby the particular type of data provided by each particular sensor is automatically recognized by the body transceiver when the respective associated autonomous sensor unit is applied to the skin or body surface of the subject. This is true regardless whether the sensor units are arranged directly adjacent one another, or at disparate locations on the body of the subject, and is achieved by means of an appropriate signal preprocessing carried out directly within each sensor unit, and through the use of a unitary interface for carrying out the subsequent data exchange of the data signal between the sensor units and the body transceiver, via the skin and other body tissues of the subject.

The basic system according to the invention, comprising sensor units, a body transceiver, and a data recorder or data logger, allows the data to be recorded in electronic memory cards, or on magnetic data carriers, or the like, or to be downloaded through an appropriate interface into a computer such as a personal computer or an onboard computer system of a space station, for carrying out further processing or evaluation. The data transmission from the body transceiver to the data logger or data recorder is carried out by telemetry, for example by a radio link, whereby the transmission range is limited to a few meters, for example less than 10 meters. The portable data logger itself can be worn on a belt or in a pocket of the clothing of the subject, for example.

The inventive system can further be integrated into a local monitoring system of a hospital or of a space station or the like. In an application in a space station, the inventive system makes it possible to carry out a continuous and global monitoring of the physical and medical condition of each astronaut, while using existing satellite communication systems for transmitting the medical and/or physical data from the space station to earth, or among plural space stations, where the monitoring is to be carried out remotely from the space station in which the subject astronauts are located. In this context, appropriate high frequency transmitter and receiver units, or infrared transmitter and receiver units, are integrated into the data logger and into the body transceiver as appropriate for carrying out the signal transmission.

The sensors integrated into the present inventive system are predominantly sensors for measuring the medical or physical conditions of the subject, for example measuring parameters such as the body temperature, the EKG, the pulse, the blood oxygen saturation, and/or the skin conductivity, of the subject. Nonetheless, additional so-called environmental sensors can also be combined into the inventive system, for example sensors adapted to measure the prevailing ambient air quality such as the oxygen content, the surrounding ambient temperature, and/or the respective location of the sensor by means of a global positioning system (GPS) or the like. Thus, the sensor data transmitted or exchanged via the skin or other body tissues of the subject are not limited to the data relating to the medical or physical condition of the subject, but instead can also provide information regarding the surroundings of the subject. All of these different types of data are received, processed, and retransmitted by the body transceiver.

Using the system according to the invention, the user can quickly and flexibly react to different monitoring functions or tasks. The autonomous sensor units are preferably embodied in a configuration resembling a typical adhesive medical bandage, so that the sensors may easily be applied to any desired location on the body of the subject without requiring any additional securing or fastening, and the sensor units can just as easily be removed when they are no longer needed. In order to achieve such mobility and miniaturization, respective microchips incorporating sensor-specific signal processing circuitry and integral data transmission circuitry are incorporated directly in the respective sensor unit. The system according to the invention is thus highly flexible, adaptable, and user-friendly, and allows the use of new sensors, as well as future developed sensors, without simultaneously requiring a modification of the other modules of the system.

As described above, the invention is suitable for use in space technology for monitoring the medical and physical conditions of astronauts. Moreover, the inventive system is especially also suitable for monitoring the physical and medical condition of ambulatory patients who do not need to be confined to a hospital or the like, but do require continuous monitoring of their condition. By using the inventive system, such patients become completely independent of the hospital or other medical facility and the previously existing telecommunication infrastructure using telephone lines and the like. The inventive system is also readily useable for all independent chronically ill or handicapped persons, as well as for monitoring persons in the field of sports medicine and work place medicine. The inventive system can be used directly within a hospital or other medical facility, to achieve a cable-free remote monitoring of patients in individual hospital rooms, hallways, operating rooms, or testing facilities, whereby a patient can be continuously monitored while the patient is transferred or moves from place to place within the overall medical facility, without requiring disconnection and reconnection of cable-based monitoring systems. The inventive system can also be directly integrated into an electronic patient data acquisition system.

Further applications of the inventive system include use by emergency medical technicians, ambulance services, search and rescue services, and catastrophic aid services, in which the system provides for the continuous monitoring of the condition of injured or sick subjects after their first aid treatment by an emergency doctor or technician. Similarly, the system is useful for mobile hospitals that are outfitted with a minimum of medical equipment and devices, yet can be connected to the assistance of medical experts anywhere in the world by means of a data exchange via satellite, by using the inventive system.

BRIEF DESCRIPTION OF THE DRAWINGS

In order that the invention may be clearly understood, it will now be described by way of example, with reference to the accompanying drawings, wherein:

FIG. 4 is a schematic block diagram of the inventive system for remote long-term medical monitoring using satellite transmission of the medical data.

DETAILED DESCRIPTION OF PREFERRED EXAMPLE EMBODIMENTS AND OF THE BEST MODE OF THE INVENTION

Figure 1:
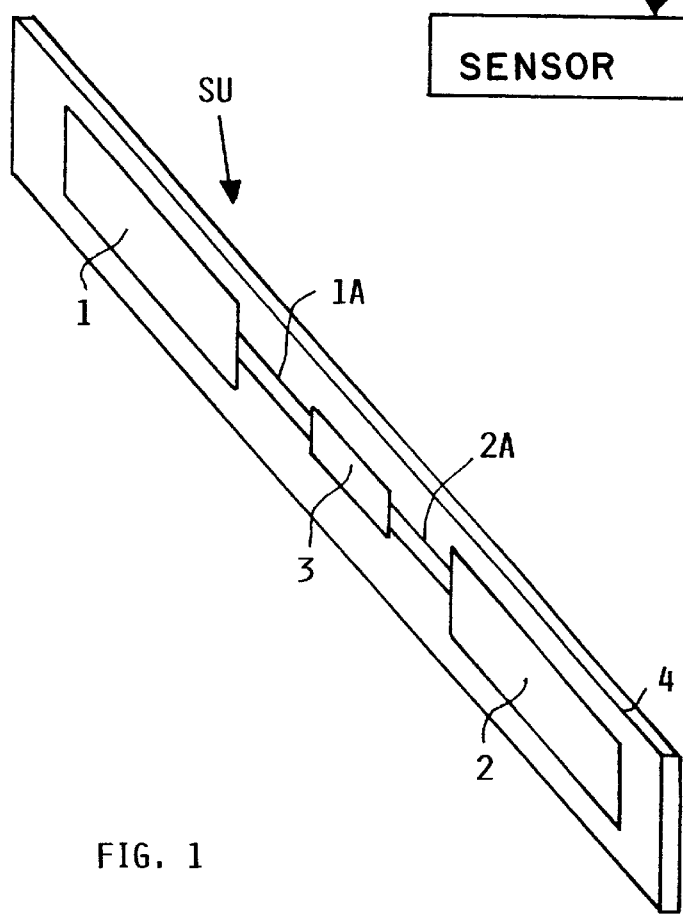
FIG. 1 is a schematic perspective view of an autonomous microsensor unit according to the invention, in the configuration of a medical bandage.

FIG. 1 schematically shows an autonomous sensor unit SU, which is a component of the present inventive system. The sensor unit SU comprises at least one miniaturized sensor 1, as well as at least one pair of transmitting and receiving electrodes 2, which are both connected to a microchip 3 by respective signal conductors 1A and 2A. This circuit arrangement is mounted on a sensor carrier or substrate 4, which is preferably in the form of a bandage 4, including an appropriate adhesive, so that the entire sensor unit SU can be adhered onto the skin of an astronaut or other subject in the manner of a typical adhesive medical bandage.

Figure 2:
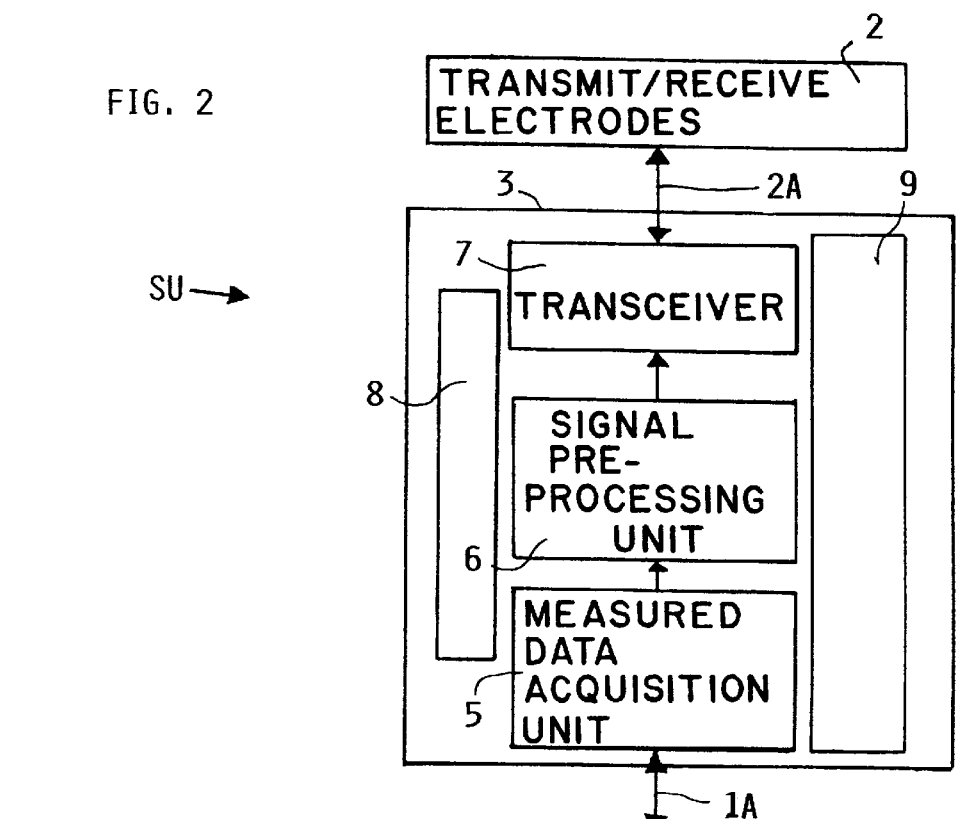
FIG. 2 is a schematic block circuit diagram of the sensor unit of FIG. 1.

The microchip 3 of the sensor unit SU is a highly integrated electronic circuit component, as particularly shown in the detail view of FIG. 2. As shown in FIG. 2, the microchip 3 includes a measured data acquisition unit 5 connected via the dataline 1A to the sensor 1, a signal preprocessing unit 6 connected downstream from the measured data acquisition unit 5, and a transceiver 7 that is connected via the signal line 2A to the transmitting and receiving electrodes 2. The microchip 3 further includes a battery 8 and a control and monitoring unit 9 for controlling and monitoring the power supply from the battery 8 to the other electronic components or circuits of the microchip 3.

The sensor 1 acquires data such as medical data from the body of the subject, or environmental data from the environment surrounding the subject as described above, and transmits this data to the measured data acquisition unit 5 via the signal line 1A. Any conventionally known sensors in this context may be used. The measured data acquisition unit 5 acquires and recognizes the data and passes it on to the signal preprocessing unit 6, wherein the signal is processed as necessary to allow it to be transmitted by the following transceiver 7. For example, the signal is processed to include a code that unambiguously identifies the type of data being transmitted (e.g. pulse data or blood oxygen data) and the particular sensor 1 that provided the data, as well as a signal component representing the data itself. Hereby, the code and the data can be processed and provided in analog or digital form. The transceiver 7 then transmits the preprocessed signal via the transmit/receive electrodes 2 into the skin and other body tissues of the subject.

The transmit/receive electrodes 2 can also receive signals through the skin and other body tissues of the subject, for example from the body transceiver that will be discussed below. Such received signals are provided to the transceiver 7, which may then take appropriate action or provide appropriate signals responsive to the received signal. For example, the received signal may be a query or polling signal or an address code signal, that particularly requests the respective identified sensor unit SU to provide its measured data at the given time. Alternatively, the received signal may be a maintenance signal that calls for the transceiver to transmit a signal indicating the remaining power level of the battery 8, or a diagnostic signal or the like. A certain degree of reprogramming or program switching in the microchip 3 can also be carried out responsively to an appropriate received signal.

Figure 3:
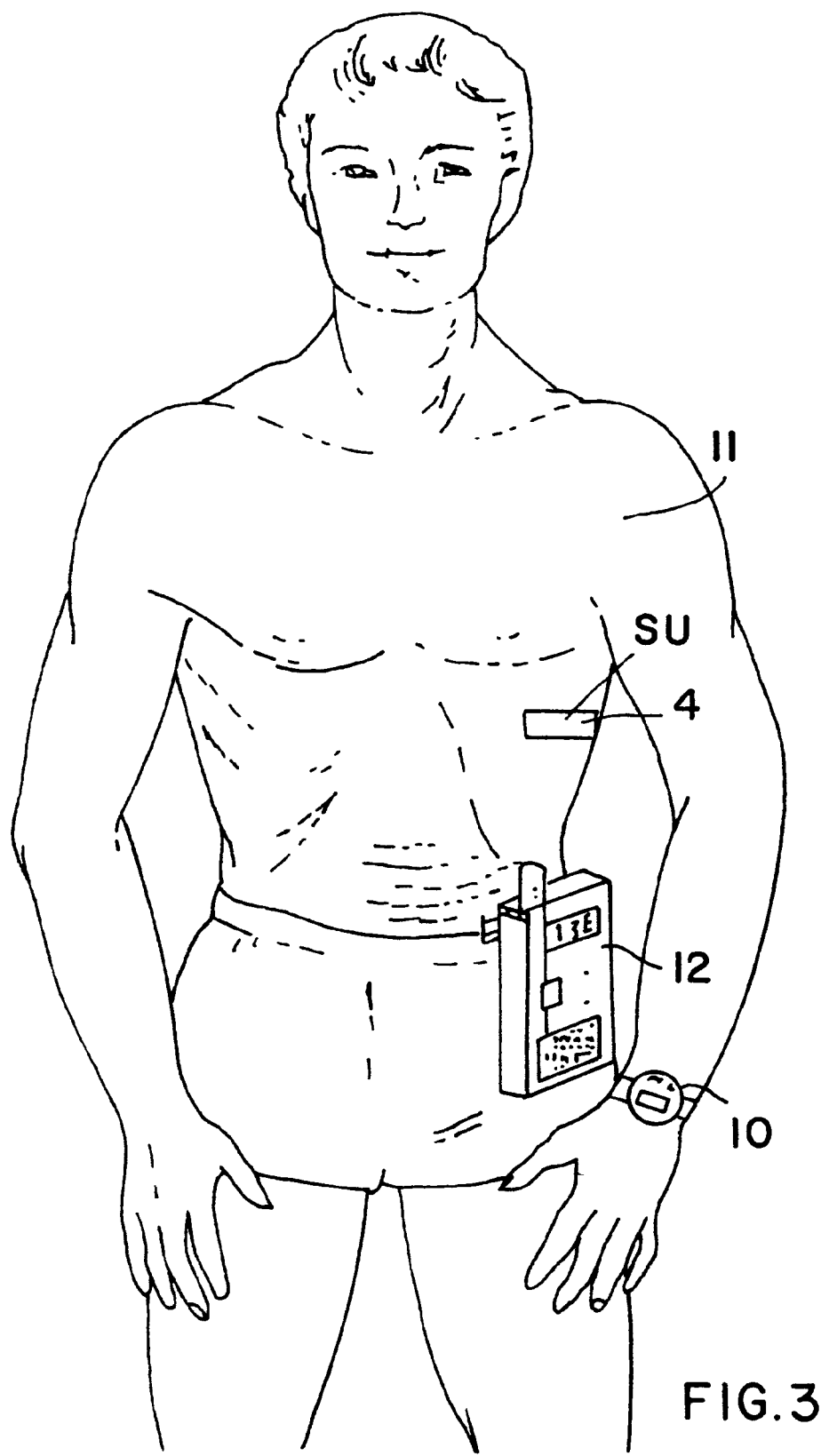
FIG. 3 is a schematic illustration of the inventive system for long-term medical monitoring as applied to an astronaut as a representative subject to be monitored.

Referring now to FIG. 3, the autonomous sensor unit SU can be seen adhered like a bandage onto the chest of a representative subject 11, for example an astronaut 11 whose medical condition is to be monitored. All that is visible of the autonomous sensor unit SU is the bandage-like backing or sensor carrier 4. It should be understood that one or more of such autonomous sensor units SU with the same sensing function or respective different sensing functions can be arranged at different locations on the body of the astronaut 11, by simply being adhered onto the skin of the astronaut 11 in the manner of an adhesive bandage.

FIG. 3 further shows a second module or component of the inventive system, namely the so-called body transceiver 10, which is embodied in the form of a wristwatch or bracelet 10 in the present example. In other words, the body transceiver 10 is worn around the wrist of the astronaut 11, while making good contact with the skin of the astronaut 11 through electrodes of the transceiver 10. The electrodes may be provided by the bracelet or armband of the transceiver 10, for example.

It is clear in FIG. 3 that there is no wire connection between the autonomous sensor unit SU and the body transceiver 10. Instead, the signals or data that are sensed by the sensor 1 are processed and transmitted in the microchip 3, and then conducted from the transmit/receive electrodes 2 into the skin and other body tissues of the astronaut 11. These signals are then conducted in the manner of alternating current electrical voltage signals through the skin and other body tissues of the astronaut 11 to the body transceiver 10 worn around the wrist of the astronaut 11. The data exchange between the autonomous sensor unit SU and the body transceiver 10 is thus carried out directly through the body tissues of the subject, i.e. the astronaut 11, and is therefore based in and confined to the body of the subject. In order to achieve good conductivity between the sensor unit SU and the body transceiver 10, any known conductive paste or the like, which are typically used when electromedical sensors are applied to a subject, can be applied between the sensor unit SU and the skin as well as between the body transceiver 10 and the skin of the subject.

The system according to the invention further includes a data logger 12, which is shown schematically being carried on the belt or in a pocket of the clothing of the astronaut 11. The data that is received and retransmitted by the body transceiver 10 are stored or recorded by the data logger 12. The data transmission connection between the body transceiver 10 and the data logger 12 can be a hard-wired electrical or optical conductor, or a radio transmit-and-receive link or an optical, e.g. an infrared transmit-and-receive link, or can be carried out through the skin and other tissues of the subject 11 as described above for the signals between the autonomous sensor unit SU and the body transceiver 10. Depending on the particular data transmission pathway between the body transceiver 10 and the data logger 12, it is not necessary that the data logger 12 must be worn or carried by the subject 11. Preferably, the data transfer from the body transceiver 10 and the data logger 12 is carried out by remote telemetry means, such as a short distance radio transmission or the like. In the data logger 12, the data may be recorded or stored in memory cards, or further processed, or further transmitted as will be discussed next.

In order to monitor and evaluate the data being received and recorded by the data logger 12, the data may later be read out or downloaded from the data logger 12 and subjected to a subsequent evaluation, including being graphically represented or printed out or the like. This can be achieved by connecting the data logger 12 to a personal computer or other computer system.

Alternatively, the data transmitted to the data logger 12 are directly retransmitted in a wireless manner by means of a high frequency radio transmission or by means of an infrared transmission. This can be carried out in any manner as schematically represented in FIG. 4.

Namely, FIG. 4 schematically indicates that data regarding the medical and physical condition of the subject 11, as well as data representing the surrounding environmental conditions, can be transmitted from the body transceiver 10 to the data logger 12, or to a base station 13, for example the space station in which the astronaut 11 is working. If the data is first provided to the data logger 12, it can be retransmitted from the data logger 12 directly to the base station 13, or via an intermediate satellite 14 to the base station 13, or via the satellite 14 to another station such as an earth-based hospital 15. The use of the intermediate satellite transmission via the satellite 14 is especially useful for completely earth-based monitoring systems. In such an application, the subject 11 and all the other equipment of the present system may be entirely terrestrially based, and the signal transmission via the satellite 14 is used to conveniently transmit the data to and from another ground-based station such as a hospital 15 in a wireless manner over unlimited distances.

As schematically indicated in FIG. 4, the data provided to the data logger 12 and/or to the base station 13 may be graphically displayed on a screen S or the like, or may be downloaded to a personal computer PC or the like, or stored in a magnetic disk D or the like. The several transmission links are all dual direction transmission links, so that a signal, for example a query or polling signal, can be transmitted from a ground-based hospital 15 or the like, via the satellite 14, to the base station 13 or to the data logger 12, which in turn sends the signal via the body transceiver 10 through the skin and other body tissues of the subject 11 to the autonomous sensor units so as to call up a data reading by the appropriate associated sensor unit SU.

Although the invention has been described with reference to specific example embodiments, it will be appreciated that it is intended to cover all modifications and equivalents within the scope of the appended claims. It should also be understood that the present disclosure includes all possible combinations of any individual features recited in any of the appended claims.

What is claimed is:

1. A system for long-term physical monitoring of a living being subject, comprising:

at least one autonomous sensor unit comprising a carrier embodied as an adhesive bandage adapted to be adhered onto the skin of the subject, a data sensor arranged on said adhesive bandage, a pair of transmitting electrodes that are arranged on said adhesive bandage and are adapted to be electrically conductingly contacted onto the skin of the subject, and a microchip that is arranged on said adhesive bandage and connected between said data sensor and said pair of transmitting electrodes;

a central transmitting and receiving unit including a pair of receiving electrodes that are adapted to be electrically conductingly contacted onto the skin of the subject at a location displaced from said autonomous sensor unit; and a portable data recording unit arranged separately from said central transmitting and receiving unit and adapted to receive an output signal from said central transmitting and receiving unit;

wherein said microchip of said autonomous sensor unit is adapted to generate an alternating current (a.c.) voltage signal as a data signal responsive to data received from said data sensor, and said transmitting electrodes of said autonomous sensor unit are adapted to transmit said data signal into the skin and body tissue of the subject to be transmitted through the skin and body tissue of the subject to said receiving electrodes of said central transmitting and receiving unit; and wherein said receiving electrodes of said central transmitting and receiving unit are adapted to receive said data signal through the skin and body tissue of the subject, and said central transmitting and receiving unit is adapted to process and retransmit said data signal as an output signal to said portable data recording unit.

2. The system according to claim 1, wherein said microchip comprises a measured data acquisition unit connected to said data sensor, a signal pre-processing unit connected to said measured data acquisition unit, and a transceiver connected to said signal pre-processing unit and to said transmitting electrodes.

3. The system according to claim 2, wherein said microchip further comprises an on-chip battery, and a control and monitoring unit adapted to control and monitor a supply of power from said battery.

4. The system according to claim 1, wherein said receiving electrodes of said central transmitting and receiving unit are further adapted to transmit second signals from said central transmitting and receiving unit into the skin and body tissue of the subject, and wherein said transmitting electrodes of said autonomous sensor unit are further adapted to receive the second signals from the skin and body tissue of the subject.

5. The system according to claim 1, wherein said data sensor is adapted to sense a medical condition parameter of the subject and provide said data corresponding thereto.

6. The system according to claim 5, wherein said data sensor comprises a sensor electrode that is adapted to be electrically conductingly contacted onto the skin of the subject and that is adapted to sense the medical condition parameter of the subject.

7. The system according to claim 5, wherein said data sensor further comprises an environmental sensor that is adapted to sense an environmental parameter of an ambient environment surrounding the subject.

8. The system according to claim 1, wherein said data sensor comprises an environmental sensor that is adapted to sense an environmental parameter of an ambient environment surrounding the subject.

9. The system according to claim 1, comprising a plurality of respective ones of said autonomous sensor unit, wherein respective ones of said data sensors of said sensor units are respectively adapted to sense respective different medical condition parameters of the subject, and wherein all of said sensor units are adapted to transmit respective ones of said data signals through the skin and body tissue of the subject to said central transmitting and receiving unit.

10. The system according to claim 1, wherein there is no wire, no optical fiber, and no radio transmission device linking said autonomous sensor unit to said central transmitting and receiving unit for transmission therebetween.

11. The system according to claim 1, wherein said central transmitting and receiving unit has a bracelet configuration and is adapted to be worn around a wrist of the subject.

12. The system according to claim 1, wherein said portable data recording unit comprises a data logger.

13. The system according to claim 1, wherein there is no physical connection between said central transmitting and receiving unit and said portable data recording unit, and wherein said central transmitting and receiving unit is adapted to transmit said data signals to said portable data recording unit by telemetry.

14. The system according to claim 1, further comprising a communications satellite orbiting the earth and an earth-based station, wherein at least one of said central transmitting and receiving unit and said portable data recording unit is adapted to transmit said output signal to said satellite, which is adapted to retransmit said output signal to said earth-based station.

15. A method of using the system according to claim 1, wherein the subject is a human astronaut, said method comprising applying said autonomous sensor unit onto the skin of the astronaut, sensing a medical condition parameter of the astronaut using said data sensor, pre-processing said parameter in said sensor unit to provide a data signal, transmitting said data signal through the skin and body tissue of the astronaut from said sensor unit to said central transmitting and receiving unit, processing said data signal in said central transmitting and receiving unit to prepare an output signal, and transmitting said output signal from said central transmitting and receiving unit to said portable data recording unit.

* * * * *